US005703122A

United States Patent [19]
Duffy

[11] Patent Number: 5,703,122
[45] Date of Patent: Dec. 30, 1997

[54] ASCORBIC ACID COMPOSITIONS FOR REDUCING IRRITATION OF TOPICALLY APPLIED ACTIVE INGREDIENTS

[75] Inventor: John A. Duffy, West Milford, N.J.

[73] Assignee: Avon Products, Inc., Suffern, N.Y.

[21] Appl. No.: 597,149

[22] Filed: Feb. 6, 1996

Related U.S. Application Data

[62] Division of Ser. No. 268,658, Jun. 29, 1994, Pat. No. 5,516,793, which is a continuation of Ser. No. 53,989, Apr. 26, 1993, abandoned.

[51] Int. Cl.$^6$ ........................................... A61K 31/34
[52] U.S. Cl. ................................................ 514/474
[58] Field of Search .................................... 514/474

[56] References Cited

U.S. PATENT DOCUMENTS

| 4,983,382 | 1/1991 | Wilmott et al. |
| 5,140,043 | 8/1992 | Darr et al. |

OTHER PUBLICATIONS

The Merck Manual, 5th Edition, 1987, Merck & Co., Rahway, NJ, pp. 2255, 2347–2350.
Sauer, Manual of Skin Diseases, 3rd Edition, 1973, J.B. Lippincott Co., Philadelphia, PA.

*Primary Examiner*—Zohreh Fay
*Attorney, Agent, or Firm*—Hopgood, Calimafde, Kalil & Judlowe L.L.P.

[57] ABSTRACT

The use of an effective amount of ascorbic acid (Vitamin C) or one or more of its derivatives, has been found to decrease skin irritation caused by the topical administration of an active ingredient for treating a skin condition. Examples of the active ingredient include α-hydroxy acids, β-hydroxy acids, keto acids, benzoyl peroxide, retinol (Vitamin A), retinoic acid, retinal $A_2$, Vitamin A epoxide, lactamides and quaternary ammonium lactates, $C_{4-12}$ hydroxylated carboxylic acids, sulfur, resorcinol and salicylic acid, and various derivatives thereof. The ascorbic acid (or its derivatives) is present in effective amounts from about 0.5% to about 25% by weight. It is provided by topical application of a separate solution or by admixture with a cosmetically or pharmaceutically acceptable vehicle for the active ingredient.

12 Claims, No Drawings

ASCORBIC ACID COMPOSITIONS FOR REDUCING IRRITATION OF TOPICALLY APPLIED ACTIVE INGREDIENTS

This is a divisional application of application Ser. No. 08/268,658 filed Jun. 29, 1994, now U.S. Pat. No. 5,516,793 which is a continuation of application Ser. No. 08/053,989, filed Apr. 26, 1993, now abandoned.

BACKGROUND OF THE INVENTION

1. Field of the Invention

This invention relates to dermatologic agents which reduce irritation caused by the topical application of an active ingredient used to treat a skin condition. More particularly, ascorbic acid or a derivative product is added to a cosmetically and/or pharmaceutically acceptable vehicle to reduce the irritation reaction.

2. State of the Art

Human skin is a complex organ which extends over the entire body. There are different types of skin at different locations on the body. For example, facial skin differs from skin on the scalp; and skin on the front (palm) of the hand is different from that on the back. Although the type of skin can vary over a person's body, skin is generally composed of two main layers of tissue. The outermost layer is the epidermis or cuticle. It is composed of three superficial and two deep layers. The derma, corium, or cutis vera, the true skin, is composed of a papillary layer above and a reticular layer below.

Since ancient times, a variety of substances have been used to improve skin appearance. Early techniques were generally directed to the outermost layer of skin, or to ailments found on the true skin. More recently, efforts have been made to rejuvenate the skin and reclaim elasticity or suppleness lost from aging and/or exposure to sunlight (UV radiation) and weather.

U.S. Pat. No. 3,897,537 describes several α-hydroxy acids, keto acids and esters thereof which are useful in the treatment of ichthyosiform dermatoses. These conditions are characterized by a fish-scale appearance typically caused by hereditary disorders. This patent contemplates daily application of a composition with at least one lower organic hydroxy acid, keto acid or esters thereof in the range from 1 to 20 weight percent.

Alpha-hydroxy acids and keto acids have also been recognized as useful for treating a number of other skin conditions. For instance, U.S. Pat. No. 3,920,835 describes a treatment for skin lesions which accompany disturbed keratinization. Examples of this condition include dandruff, acne, palmar and plantar (hand and foot) hyperkeratosis and palmar and plantar callouses which are secondary manifestations of eczema or chronic friction. For additional disclosures, please see U.S. Pat. Nos. 3,984,566 and 3,988,470.

Acne (acne vulgaris) is a very common condition for which a variety of prescription and over-the-counter remedies are available. Benzoyl peroxide is a common over-the-counter remedy. But, the active ingredient is a strong oxidizing agent which may cause allergic or dermatitic reactions. U.S. Pat. No. 4,021,572 describes the use of lactamides and quaternary ammonium lactates for acne treatment. Lactic acid is a useful, but potentially irritating compound. Non-irritating compositions are formed when lactic acid is first reacted with a suitable base, such as ammonium hydroxide or an alkyl amine. The condition of dry skin is characterized by cracking, flaking and/or scaling. U.S. Pat. No. 4,105,733 describes the treatment of this condition with free acids, or the amide and/or ammonium salts of selected acids, including α-hydroxy and keto acids.

U.S. Pat. Nos. 4,363,815; 4,380,549 and 5,091,171 should also be noted for their various disclosures of α-hydroxy and/or keto acids and various derivatives for the treatment of multiple ailments. Exemplary derivatives of these compounds include the peroxide, amide, lactone, anhydride, ester and polymeric forms, as well as various organic or inorganic salts. Known acids and/or their derivatives may be combined with amphoteric compounds (such as peptides and polypeptides) or pseudoamphoteric compounds (such as creatinine). In addition to the skin conditions already mentioned, these compositions are useful for treating psoriasis, pruritus, age spots, melasmas, wrinkles, warts, blemishes, hyperpigmentation, inflammatory dermatoses and the like.

Compositions which reduce dryness or flakiness and improve the suppleness or smoothness of skin are also known in the art. These compositions comprise effective amounts of an hydroxylated carboxylic acid having 4–12 carbon atoms, in combination with a cosmetically acceptable vehicle other than water—which is not excluded, but another vehicle must be present.

Additional acne medications are available for use over-the-counter. These formulations typically contain sulfur, resorcinol, salicylic acid and benzoyl peroxide or combinations thereof. Recent products include retinol (Vitamin A) and various derivatives, such as retinoic acid, also known as tretinoin and Retin-A, have been used for the treatment of severe acne. See, for example, U.S. Pat. No. 3,006,939 which relates to retinoic acid; and U.S. Pat. No. 4,826,828 which describes the preparation of stable retinol compositions, especially for reducing wrinkles.

U.S. Pat. Nos. 3,932,665 and 4,934,114 disclose the use of retinal (Vitamin A aldehyde) for the treatment of acne and skin keratoses, respectively. U.S. Pat. No. 3,060,229 also illustrates the state of this art. Retinal and it derivatives have found application in the treatment of wrinkles, warts, psoriasis, eczema, dandruff and like conditions (EP-A2-0 391 033). There are also suggestions that tretinoin can heal or reverse the effects of photoaging. Representative publications include Kligman, "Current Status of Topical Tretinoin in the Treatment of Photoaged Skin," *Drugs & Aging*, 2(1):7–13 (1992); Ellis, "Tretinoin: Its Use in Repair of Photodamage," and Zelickson, "Topical Tretinoin in Photoaging: An Ultrastructural Study," both presented in the *Journal of Cutaneous Aging & Cosmetic Dermatology*, Vol. 1, No. 1, pp. 33–40 and 41–47 (1988).

Vitamin C (ascorbic acid) and its derivatives are other compounds which have been topically applied as the active ingredient for the treatment of various skin conditions. U.S. Pat. No. 4,983,382 describes the preparation of stabilized ascorbic acid compositions for topical application. See also, U.S. Pat. Nos. 5,140,043 and 5,122,536 which describe the use of ascorbic acid for preventing ultraviolet radiation damage and treating psoriasis.

With these and other known ingredients, end-users may suffer from irritation or dermatitis due to the active ingredient, the vehicle or a combination of both. The source of these dermatoses is not always the same, and the reason is not always apparent. For example, a skin rash may result because the active ingredient or vehicle causes a dry condition similar to the action of soap. Irritation may also arise from the transdermal administration of an active ingredient.

And, the conformational and/or stereochemistry of the active ingredient may induce an allergic-type irritation.

It will be appreciated that any irritation caused by treatment for a given skin condition is undesirable. These conditions typically have a non-aesthetic appearance, which is often the reason a patient seeks treatment in the first instance. Poor aesthetic appearance of the skin may be (or may appear to be) aggravated by treatment when irritation is caused by the active ingredient. Adverse cosmetic reactions may worsen with continuing use of a particular active ingredient over an extended period of time. These negative results can be quite disturbing to the patient. And, they may prompt a patient to discontinue treatment or neglect the original condition. The end-user or physician may reduce the number of treatments or lower the concentration of active ingredient (again reducing the effectiveness of treatment).

Therefore, it would be desirable to reduce or eliminate irritation resulting from the treatment of skin conditions, regardless of whether this condition is caused by the active ingredient, the vehicle or some combination thereof.

It may also be desirable to topically apply higher concentrations of active ingredient for better efficacy or to enhance the effect of a pre-selected active ingredient, thereby permitting less frequent or less concentrated administration of the active ingredient.

SUMMARY OF THE INVENTION

It is an object of the present invention to provide a topically applied dermatological agent which eliminates or reduces the occurrence of irritation which may accompany treatment of a skin condition.

It is another object of the present invention to provide a topically applied dermatological agent which includes higher concentrations of active ingredients used to treat a variety of skin conditions.

A further object of the present invention is to provide a topically applied dermatological agent with improved efficacy.

Yet another object of the present invention is to provide a topically applied dermatological agent which exhibits shorter response time for absorption and clearance (dissipation) into several layers of skin.

It is still another object of the present invention to provide a cosmetically or pharmaceutically acceptable vehicle which enhances the effect of an active ingredient, thereby permitting lower concentrations of active ingredient and reducing possible incidence of irritation.

In brief, then, the invention generally provides a dermatological agent which includes an active ingredient and a cosmetically or pharmaceutically acceptable vehicle. This dermatological agent comprises an amount of ascorbic acid, or a derivative thereof, effective to reduce irritation caused by the composition topically administered to the patient.

This invention also provides a separate topical vehicle which includes at least one inert composition and an amount of ascorbic acid, or its derivatives, effective to reduce irritation caused by the active ingredient or vehicle, or a combination thereof.

Still further, this invention provides a method for reducing skin irritation which comprises the topical application of an active ingredient with an amount of ascorbic acid (or a derivative thereof) which is effective to reduce irritation caused by the active ingredient or other constituents. The ascorbic acid composition and active ingredient may be combined in a cosmetically or pharmaceutically acceptable vehicle, or the ascorbic acid composition and active ingredient may be topically applied in separate solutions.

DETAILED DESCRIPTION OF SPECIFIC EMBODIMENTS

As just summarized, this invention is generally directed to dermatological agents which include an active ingredient used to treat a skin condition and an amount of ascorbic acid, or a derivative thereof, effective for reducing irritation. While this specification is primarily directed to illustrating the invention with respect to active ingredients which induce irritation, it should be appreciated that irritation may be caused by the vehicle (without the ascorbic acid) or by a combination thereof.

The active ingredient may be any of those described in the admitted references which are incorporated by reference herein, or any other active ingredient which is administered in a topical formulation. The presence of ascorbic acid reduces the occurrence or severity of irritation and/or provides for higher concentrations of active ingredient without causing irritation. The present invention contemplates the use of compounds which release or convert to ascorbic acid and/or its derivatives when topically applied or administered to skin. Derivatives of ascorbic acid include pharmaceutically and dermatologically acceptable salts, esters, reverse esters and anhydrides. Examples include alkali salts such as sodium ascorbate (U.S. Pat. No. 2,442,005, incorporated by reference herein) and potassium ascorbate; alkaline earth salts such as calcium ascorbate (U.S. Pat. Nos. 2,596,103 and 2,442,461, incorporated by reference herein); magnesium ascorbate and compatible mixtures. Exemplary esters include ascorbyl palmitate, ascorbyl laureate, ascorbyl myristate, ascorbyl stearate and compatible mixtures. Other salts, such as magnesium ascorbyl phosphate, are also suitable.

In general, ascorbic acid and/or any derivative thereof will be present in amounts of at least about 0.5%, more preferably at least about 5%, and most preferably at least about 10% based on the weight of the composition (all percentages are expressed on a weight basis unless otherwise noted). The ascorbic acid or derivative compound is preferably present in effective amounts of not more than about 25%, more preferably in amounts of not more than about 20%, and most preferably in amounts of not more than about 15%.

In addition to ascorbic acid and/or derivative(s), the dermatological agent includes at least one inert vehicle which should be essentially hypoallergenic. That is, the vehicle should not induce adverse effects on the skin or aggravate the condition being treated. The vehicle should not deactivate the ascorbic acid, its derivatives or the active ingredient by chemical alteration of a constituent compound or by interference with the absorption or action of a constituent compound.

Suitable inert vehicles can be identified from the literature or by routine experimentation. They may be simple solutions (e.g., isotonic saline), or emulsified mixtures including one or more components selected from water, organic solvents, oils, emulsifiers and the like. The vehicle should be chosen for its ability to solubilize or disperse both the ascorbic acid (including derivatives as may be present) and the active ingredient.

Exemplary vehicles include water (preferably distilled or demineralized), alcohol (e.g., ethanol, isopropanol), propylene glycol, glycerin and mixtures thereof as the diluent. Ascorbic acid and its derivatives, as well as many dermatologic agents, are solid at ambient temperature and demonstrate varying degrees of solubility in water, oils and organic solvents. For topical application, ascorbic acid and the active ingredient are solubilized in the vehicle. If necessary, an emulsifier or surfactant may be used to facilitate solubilization of ascorbic acid or the active ingredient.

The dermatological agent may also include conventional adjuvants, such as viscosity modifying agents, preservatives, humectants, demulcents, moisturizers, colorants, fragrances and compatible mixtures thereof. Exemplary viscosity modifying agents include hydroxylpropyl cellulose and carboxymethyl cellulose. Antioxidants or preservatives may include any compositions which are readily available and well known in the art.

The formulation may also include a dispersant for one or more of the components, such as a colorant or fragrance. Suitable dispersants include various polyhydric alcohol anhydride partial higher fatty acid esters, e.g., Span 20, sorbitan monolaurate; Span 40, sorbitan monopalmitate; Span 60, sorbitan monostearate; Span 65, sorbitan tristearate; Span 80, sorbitan monooleate; Span 85, sorbitan trioleate or similar compounds, including Tween 20, sorbitan monolaurate polyoxyalkylene; Tween 40, sorbitan monopalmitate polyoxyalkylene; Tween 65, polyoxyethylene sorbitan tristearate and the like.

The novel vehicle thus comprises at least one inert composition in combination with an effective amount of ascorbic acid and/or derivative(s) thereof, formulated for topical administration of a dermatologically active ingredient.

The active ingredient may be any of those noted in this specification including, without limitation, α-hydroxy acids, keto acids, Vitamin A and derivatives thereof, salicylic acid, hydroquinone (for skin lightening) and compatible mixtures thereof. Suitable α-hydroxy acids, and related acids such as β-hydroxy acids, generally have two to six carbon atoms. Examples include glycolic acid, lactic acid, citric acid, malic acid, tartronic acid, tartaric acid, glycuronic acid, pyruvic acid, 2-hydroxyisobutyric acid, 3-hydroxybutyric acid, and derivatives thereof, such as esters and reverse esters with alcohols having one to six carbon atoms (e.g., methyl pyruvate). Other active ingredients include Vitamin $A_2$ (3,4-didehydroretinol), hepaxanthin (Vitamin A epoxide; 5,6-epoxy-5,6-dihydroretinol) and additional derivative compounds. See, for example, the Food and Drug Administration's Final Monograph for Topical Acne Products for Over-the-Counter Human Use, *Federal Register*, Vol. 56, No. 159 (1991).

Prior to illustrating the invention with specific examples, the assay for testing degrees of irritation and/or dermatitis will be described.

Irritation Assay

The testing universe includes twenty (20) female subjects. A particular formulation is applied to a large area of skin twice daily for seven (7) consecutive days. Observations of the skin are recorded daily, as well as at the end of the seven day period.

The types of irritation response include, alone or in combination, symptoms such as papules, pustules, tiny pinpoint bumps or larger individual bumps. Diffuse erythema (unusual redness due to capillary congestion) is normally present with a widespread follicular response, although it may be the sole expression of irritation. The following categories of irritation patterns were possible during testing of the novel formulations of this invention.

Response Type 1. A few (e.g., 2–4) scattered papules-pustules over the treatment site, or a few (e.g., 1–3) bumps which persist for only a short duration, in which there is no subjective discomfort. The papules-pustules may dissipate with continued application of the formulation being tested; or they may persist, without additional occurrences, until completion of the testing.

Response Type 2. Various forms of erythema with or without papular-pustular/bump responses such as (i) diffuse, minimal erythema throughout the treatment site, (ii) tiny, pinpoint flat erythematous dots or (iii) erythematous patches. None of these responses are considered significant unless they are persistent, associated with subjective discomfort or clearly more severe than a Type 1 response.

Response Type 3. This type of response is characterized by numerous, tiny pinpoint bumps covering the treatment site larger individual bumps (about 10 to about 30 of varied sizes), accompanied by several papules and/or pustules. Erythema may be specific to the bumps or may be diffuse throughout the entire region. This type of response is normally accompanied by severe itching which does not dissipate. The response itself, as well as the subjective discomfort, intensifies with continued use of the formulation. This type of response is characterized as a significant reaction.

The present invention will now be described in connection with the following examples.

EXAMPLE I

Glycolic acid is an α-hydroxy acid known to improve certain skin disorders such as dry skin, ichthyosis and acne. It is also useful for healing photodamaged skin. High concentrations (e.g., 10%) of glycolic acid are effective for treating these disorders. But, glycolic acid can cause significant irritation at these concentrations. This irritation is characterized by bumps, papules, pustules and erythema, and/or a stinging or similarly uncomfortable sensation. To evaluate the present invention, the following dermatological agents were prepared.

| Ingredients | Composition A | Composition B | Function |
|---|---|---|---|
| Demineralized Water | 10.713 | 5.713 | diluent |
| Alcohol | 57.562 | 57.562 | diluent |
| Hydroxypropyl Cellulose | 0.500 | 0.500 | thickener |
| Propylene Glycol | 20.000 | 21.000 | diluent |
| Butylated Hydroxytoluene | 0.200 | 0.200 | antioxidant |
| Color Solution | 0.025 | 0.025 | color |
| Glycolic Acid | 10.000 | 10.000 | active ingredient |
| Ascorbic Acid | — | 5.000 | vehicle additive |
| | 100.000 | 100.000 | |

The pH for Compositions A and B was approximately 2.4. Both compositions were evaluated by the irritation assay described above. Each composition was applied twice daily to 20 subjects for seven days. Two of the Composition A subjects demonstrated Type 3 irritation responses. In addition, one subject reported discomfort. For the 20 subjects using Composition B, no irritation responses were recorded and none of the subjects experienced discomfort.

EXAMPLE II

The general procedure of Example I was repeated using glycolic acid partially neutralized with ammonium hydroxide in the following formulations.

| Ingredient | C | D | E | F | Function |
|---|---|---|---|---|---|
| Demin. Water | 92.516 | 86.519 | 80.920 | 74.320 | Diluent |
| Propylene Glycol | 4.000 | 4.000 | 4.000 | 4.000 | Diluent |
| Glycerin | 2.000 | 2.000 | 2.000 | 2.000 | Diluent |
| Hydroxyethyl Cellulose | 1.200 | 1.200 | 1.200 | 1.200 | Thickener |
| Fragrance | 0.030 | 0.030 | 0.030 | 0.030 | |
| Tween 20 Dispersant | 0.150 | 0.150 | 0.150 | 0.150 | |
| Citric Acid Modifier | 0.005 | — | — | — | pH |
| Amm. Hydrox | — | 2.101 | 2.700 | 4.300 | |
| Glycolic Acid | — | 4.000 | 4.000 | 4.000 | |
| Ascorbic Acid | — | — | 5.000 | 10.000 | |
| | 100.000 | 100.000 | 100.000 | 100.000 | |

The pH for Composition C was 5.08; 3.9 for Composition D; 3.7 for Composition E and 3.8 for Composition F. Using the irritation assay described above, the ability of ascorbic acid to inhibit glycolic acid-induced irritation was evaluated.

The placebo, Composition C, did not elicit any Type 3 irritation response or discomfort. This result demonstrated suitable inertness of the vehicle.

Of the ten (10) subjects using Composition D, four (4) demonstrated Type 3 irritation response. Accordingly, the presence of 4% glycolic acid in the inert vehicle induces significant irritation.

Of the twenty (20) subjects using Composition E, four (4) demonstrated a Type 3 irritation response. These results confirm the unexpected ability of 5% ascorbic acid to avoid the irritation caused by glycolic acid.

Of the twenty (20) subjects using Composition F, two (2) displayed a Type 3 irritation response. These results demonstrate the unexpected ability of 10% ascorbic acid to further reduce the incidents of irritation caused by the active dermatologic ingredient.

The results achieved with the present invention are summarized in Table 1 which is set forth below.

| Composition | % Glycolic Acid | % Ascorbic Acid | % of Subjects Tested Showing Type 3 Irritation |
|---|---|---|---|
| C | 0.0 | 0.0 | 0.0 |
| D | 4.0 | 0.0 | 40.0 |
| E | 4.0 | 5.0 | 20.0 |
| F | 4.0 | 10.0 | 10.0 |

These results clearly show that ascorbic acid is unexpectedly useful in preventing irritation caused by topically applied active ingredients.

As an alternative embodiment of the present invention, the ascorbic acid is applied separately (rather than as a part of the vehicle). For example, a solution of ascorbic acid may be sprayed onto the skin before and/or after topical application of the active ingredient.

Such a method for reducing irritation would be especially useful in connection with preformulated compositions, such as over-the-counter products. The user of such a product may immediately experience an occurrence of irritation, or irritation may become manifest after repeated use of the product. Rather than reformulating an existing over-the-counter product, a solution of ascorbic acid in a suitable dispenser (e.g., a pump spray bottle) can be applied before and/or after use of the over-the-counter product.

In another embodiment, a solution of ascorbic acid can be admixed with a pre-formulated medication (for example, a prescription drug) just prior to topical administration of the combined solution.

The descriptions and examples presented in this specification are meant to illustrate the invention without limiting effect. Various modifications and alterations to the present invention may be appreciated based on a review of this disclosure. These changes and additions are intended to be within the scope and spirit of this invention as defined by the following claims.

What is claimed is:

1. A dermatological composition which comprises an active ingredient selected from the group consisting of retinoids, salicylic acid, benzoyl peroxide, α-hydroxy acids, keto acids, hydroquinone and compatible mixtures thereof, in an amount effective for treating a skin condition, and an ascorbic acid component selected from the group consisting of ascorbic acid, alkali ascorbates, alkali earth ascorbates, ascorbate esters, ascorbyl-phosphoryl-cholesterol, ascorbate anhydrides and compatible mixtures thereof, in an amount effective for reducing irritation induced by said active ingredient, said active ingredient and said ascorbic acid component being admixed in a cosmetically or pharmaceutically acceptable vehicle.

2. The dermatological composition as defined by claim 1, wherein said vehicle is selected from the group consisting of water, propylene glycol, ethanol, propanol, glycerin, polyvinyl alcohol, and mixtures thereof.

3. The dermatological composition as defined by claim 1, further comprising at least one adjuvant selected from the group consisting of viscosity modifiers, preservatives, colorants, fragrances, humectants, demulcents, and compatible mixtures thereof.

4. The dermatological composition as defined by claim 1, wherein the ascorbic acid is present in an effective amount of at least about 0.5% by weight of the dermatological composition.

5. The dermatological composition as defined in claim 4, wherein the ascorbic acid is present in an effective amount of not more than about 25% by weight of the dermatological composition.

6. The dermatological composition as defined by claim 1, wherein the ascorbic acid is present in an effective amount of at least about 5% by weight of the dermatological composition.

7. The dermatological composition as defined in claim 6, wherein the ascorbic acid is present in an effective amount of not more than about 20% by weight of the dermatological composition.

8. The dermatological composition as defined by claim 1, wherein the ascorbic acid is present in an effective amount of at least about 10% by weight of the dermatological composition.

9. The dermatological composition as defined by claim 8, wherein the ascorbic acid is present in an effective amount of not more than about 15% by weight of the dermatological composition.

10. A topical composition for use with a topically applied active ingredient selected from the group consisting of retinoids, salicylic acid, benzoyl peroxide, α-hydroxy acids, keto acids, hydroquinone and compatible mixtures thereof, said composition comprising an inert vehicle and an ascorbic acid component selected from the group consisting of ascorbic acid, alkali ascorbates, alkali earth ascorbates, ascorbate esters, ascorbyl-phosphoryl-cholesterol, ascorbate anhydrides and compatible mixtures thereof, in an amount effective to reduce irritation caused by said active ingredient.

11. The composition as defined by claim 10, wherein said inert vehicle is selected from the group consisting of water, propylene glycol, ethanol, propanol, glycerin, polyvinyl alcohol, and compatible mixtures thereof.

12. The composition as defined by claim 10, further comprising at least one adjuvant selected from the group consisting of viscosity modifiers, preservatives, colorants, fragrances, humectants, demulcents, and compatible mixtures thereof.

* * * * *

UNITED STATES PATENT AND TRADEMARK OFFICE
CERTIFICATE OF CORRECTION

PATENT NO. : 5,703,122

DATED : December 30, 1997

INVENTOR(S) : John A. Duffy

It is certified that error appears in the above-identified patent and that said Letters Patent is hereby corrected as shown below:

Col. 8, line 37, after "ascorbic acid" insert "component".

Col. 8, line 41, after "ascorbic acid" insert "component".

Col. 8, line 45, after "ascorbic acid" insert "component".

Col. 8, line 49, after "ascorbic acid" insert "component".

Col. 8, line 53, after "ascorbic acid" insert "component".

Col. 8, line 57, after "ascorbic acid" insert "component".

At Col. 10, line 6, add:

13. The dermatological composition as defined by claim 1, wherein the ascorbic acid component is selected from the group consisting of sodium ascorbate, potassium ascorbate, calcium ascorbate, magnesium ascorbate, ascorbyl palmitate, ascorbyl laureate, ascorbyl myristate, ascorbyl stearate, magnesium ascorbyl phosphate, and compatible mixtures thereof.

UNITED STATES PATENT AND TRADEMARK OFFICE
CERTIFICATE OF CORRECTION

PATENT NO. : 5,703,122
DATED : December 30, 1997
INVENTOR(S) : John A. Duffy

It is certified that error appears in the above-identified patent and that said Letters Patent is hereby corrected as shown below:

14. The composition as defined by claim 10, wherein the ascorbic acid component is selected from the group consisting of sodium ascorbate, potassium ascorbate, calcium ascorbate, magnesium ascorbate, ascorbyl palmitate, ascorbyl laureate, ascorbyl myristate, ascorbyl stearate, magnesium ascorbyl phosphate, and compatible mixtures thereof.

Signed and Sealed this

Twelfth Day of January, 1999

Attest:

Attesting Officer

*Acting Commissioner of Patents and Trademarks*